(12) United States Patent
Li et al.

(10) Patent No.: US 9,510,624 B2
(45) Date of Patent: Dec. 6, 2016

(54) DISPOSABLE ELECTRONIC CIGARETTE

(75) Inventors: Yonghai Li, Shenzhen (CN); Zhongli Xu, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 330 days.

(21) Appl. No.: 14/343,044

(22) PCT Filed: Aug. 7, 2012

(86) PCT No.: PCT/CN2012/079776
§ 371 (c)(1),
(2), (4) Date: Mar. 5, 2014

(87) PCT Pub. No.: WO2013/034039
PCT Pub. Date: Mar. 14, 2013

(65) Prior Publication Data
US 2014/0196718 A1 Jul. 17, 2014

(30) Foreign Application Priority Data
Sep. 5, 2011 (CN) ............... 2011 2 0329988 U

(51) Int. Cl.
*A24F 47/00* (2006.01)
*A61M 11/00* (2006.01)
(Continued)

(52) U.S. Cl.
CPC ............ *A24F 47/008* (2013.01); *A61M 11/041* (2013.01); *A61M 11/042* (2014.02);
(Continued)

(58) Field of Classification Search
CPC .. A61M 11/041; A61M 11/042; A61M 15/06; A61M 2205/3653; A61M 2205/583; A61M 2205/8206; A24F 47/008
See application file for complete search history.

(56) References Cited

U.S. PATENT DOCUMENTS

2012/0145169 A1* 6/2012 Wu .................. A24F 47/008
131/273

FOREIGN PATENT DOCUMENTS

| CN | 201238610 Y | 5/2009 |
| CN | 201491720 U | 6/2010 |

(Continued)

*Primary Examiner* — Bradley Philips
(74) *Attorney, Agent, or Firm* — Cheng-Ju Chiang

(57) ABSTRACT

The present disclosure relates to a disposable electronic cigarette. The disposable electronic cigarette includes a housing, a battery assembly and an atomization device. The housing is hollow, and defines openings at two opposite ends. The battery assembly and the atomization device are connected, and disposed inside the housing. The atomization device includes a liquid absorption member, a glass fiber tube, an electrical heating component and a liquid stopper. The electrical heating component further includes a heating wire and a liquid-conducting core. The battery assembly includes a cell core, a controller and an LED lamp. A lampshade is provided on a first end of the housing, and a mouthpiece cover is arranged at a second end of the housing. The beneficial effects are that the battery assembly and atomization device are provided inside the housing to form one piece, avoiding assembling before smoking.

15 Claims, 19 Drawing Sheets

(51) Int. Cl.
   *A61M 15/00*   (2006.01)
   *A61M 11/04*   (2006.01)
   *A61M 15/06*   (2006.01)

(52) U.S. Cl.
   CPC ..... *A61M 15/06* (2013.01); *A61M 2205/3653* (2013.01); *A61M 2205/583* (2013.01); *A61M 2205/8206* (2013.01)

(56) References Cited

FOREIGN PATENT DOCUMENTS

| | | |
|---|---|---|
| CN | 101869356 A | 10/2010 |
| CN | 201830900 U | 5/2011 |
| CN | 202262413 U | 6/2012 |
| JP | 2011-87569 A | 5/2011 |
| WO | 2009/155734 A1 | 12/2009 |

* cited by examiner

DISPOSABLE ELECTRONIC CIGARETTE

CROSS REFERENCE TO RELATED APPLICATIONS

The present application is a 35 U.S.C. §371 National Phase conversion of International (PCT) Patent Application No. PCT/CN2012/079776, filed on Aug. 7, 2012, the disclosure of which is incorporated by reference herein. The PCT International Patent Application was filed and published in Chinese.

1. TECHNICAL FIELD

The present disclosure relates to electronic cigarettes, and more particularly, to a disposable electronic cigarette.

2. DESCRIPTION OF RELATED ART

Cigarettes, as addiction articles, are widely loved by people, especially men. However, the tar in the cigarettes is harmful to the health of the human body. Dozens of ingredients of the tar are carcinogenic. Furthermore, the second hand smoke is also very harmful to non-smokers. Therefore, the smoking is prohibited in most public places. However, it is not easy for the smoker to stop smoking. Thus, a lot of tobacco substitutes appear on the market. The most common tobacco substitute is a non-combustible electronic atomization cigarette, which does not contain harmful tar.

Currently, most electronic cigarettes on the market are rechargeable, refillable, and repeatedly used. Further, an atomization device and a battery assembly of this kind of electronic cigarette are separate. In use, the atomization device and the battery assembly should be first assembled. This causes a lot of inconvenience. For example, the user needs to take a charger, tobacco liquid, and a tool for filling the tobacco liquid when travelling. Before use, the user needs to assemble the atomization device and the battery assembly first. Usually, it is inconvenient to charge and fill the tobacco liquid on journey. This makes men who often travel inconvenient. Furthermore, the electronic cigarette has a complicated structure, and it is inconvenient to assemble, and unsuitable for mass production, rendering the cost the electronic cigarette is relatively high. Accordingly, it is unsuitable for promotion and widespread use.

SUMMARY

An object of the disclosure is to provide a simple, convenient disposable electronic cigarette.

According to one aspect of the present disclosure, a disposable electronic cigarette includes a housing, a battery assembly, and an atomization device. The housing is hollow and includes openings at two opposite ends thereof. The battery assembly and the atomization device are connected and disposed in the housing.

Since the battery assembly and the atomization device are arranged in the housing, forming a one-piece electronic cigarette, it is no need to assemble the battery assembly and the atomization device before smoking. The disposable electronic cigarette can be produced in large quantity.

In some embodiments, the atomization device includes a liquid absorption member, a glass fiber tube, an electrically heating component and a liquid stopper. The glass fiber tube is hollow and defines openings at two opposite ends thereof. The atomization device further includes a hollow protruding rod. The protruding rod is arranged at a first end of the liquid stopper. The protruding rod defines a through hole, and the through hole extends through the liquid stopper. The stopper includes a protruding stage at a second end thereof. The liquid stopper defines a groove along a circumferential direction thereof. The electrically heating component is mounted to the glass fiber tube. A first end of the glass fiber tube is connected with the protruding rod of the liquid stopper, and an outer surface of the glass fiber tube is wrapped with the liquid absorption member.

The advantage is securing the electrical heating component. Furthermore, the hollow protruding rod facilitates the flow of air, makes the smoking smoother. The design of the groove resolves the problem of the falling of the liquid absorption member and the liquid leakage from the atomization device to the battery assembly. The protruding stage makes the smoking smoother.

In some embodiments, the atomization device includes a liquid tank, a liquid guide, an electrically heating component, and a liquid stopper. The liquid guide includes a liquid tank cushion, and a cotton cloth. The liquid tank is disposed on the liquid tank cushion, the liquid tank cushion is arranged on the cotton cloth, and the cotton cloth is disposed on the liquid stopper. The liquid tank defines an opening at an end thereof. The liquid stopper is airtight connected to the end of the liquid tank. The electrically heating component is arranged at the end of the liquid tank, and engaged in the liquid stopper.

Since the electrically heating component is arranged at the end of the liquid tank with the opening, the electrical heating component can be in fully contact with the tobacco liquid In some embodiments, the liquid stopper defines wire holes at two opposite sides of the protruding rod.

This facilitates the connection between conductive wires and the battery assembly.

In some embodiments, the protruding rod and the liquid stopper are integrally formed.

Thus, the structure of disposable electronic cigarette is simple, and it is convenient to assemble the disposable electronic cigarette.

In some embodiments, the electrical heating component includes a heating wire, and a liquid-conducting core. The heating wire is spirally wound around the liquid-conducting core. Two ends of the liquid-conducting core pass through a sidewall of the glass fiber tube, and then extend outwardly in a horizontal direction. Two ends of the heating wire are connected to conductive wires. The conductive wires pass through the wire holes of the liquid stopper, and connect to the battery assembly.

The advantage is that the liquid-conducting core is heated by resistance heating to vaporize tobacco liquid in the atomization device.

In some embodiments, the liquid-conducting core has a rod-shaped structure, a U-shaped structure, or an S-shaped structure.

The advantage is that more liquid is conveyed by increasing area of the liquid-conducting core.

In some embodiments, the liquid absorption member has a structure of fibrous mesh.

The advantage is to prevent tobacco liquid from leaking. Further, the liquid-conducting core is in fully contact with the tobacco liquid.

In some embodiments, the battery assembly includes a cell core, a controller, and an LED lamp. A first end of the cell core is connected with the liquid stopper, and a second end of the cell core is connected with the controller. The LED lamp is disposed on the controller.

After sensing the entrance of air, the controller activates the cell core, and then the electrically heating wire and the LED lamp are powered on. The liquid-conducting core is heated to vaporize tobacco liquid, generating aerosol. The LED lamp emits light simulating smoking flame.

In some embodiments, the electronic cigarette further includes a controller holder. The controller is arranged in the controller holder, and the controller holder is arranged at the second end of the cell core.

The advantage is to protect the LED lamp and the controller.

In some embodiments, the electronic cigarette further includes a lampshade at a first end of the housing. The lampshade defines slots in side surface thereof.

The advantage is to protect the LED lamp and the controller. The slots in the lampshade facilitate the flow of air.

In some embodiments, the lampshade and the controller holder are integrally formed.

The integration of lampshade and the controller holder facilitates the placement of the controller.

In some embodiments, the electronic cigarette further includes a mouthpiece cover arranged at a second end of the housing. The mouthpiece cover defines a suction hole, and the suction hole faces a second end of the glass fiber tube.

The suction cover prevents tobacco liquid from being inhaled into the mouth of the user. The suction hole communicates with the glass fiber tube, so that aerosol can reach the mouth of the smoker.

In some embodiments, the housing is made of metal or plastic.

The housing made of different materials can satisfy demand of different users.

In some embodiments, a diameter of the cell core is less than that of the housing.

A gap between the cell core and the housing facilitates the flow of air.

DETAILED DESCRIPTION

Some embodiments of the present invention will be further described in detail accompanying the drawings below.

Figure 1:
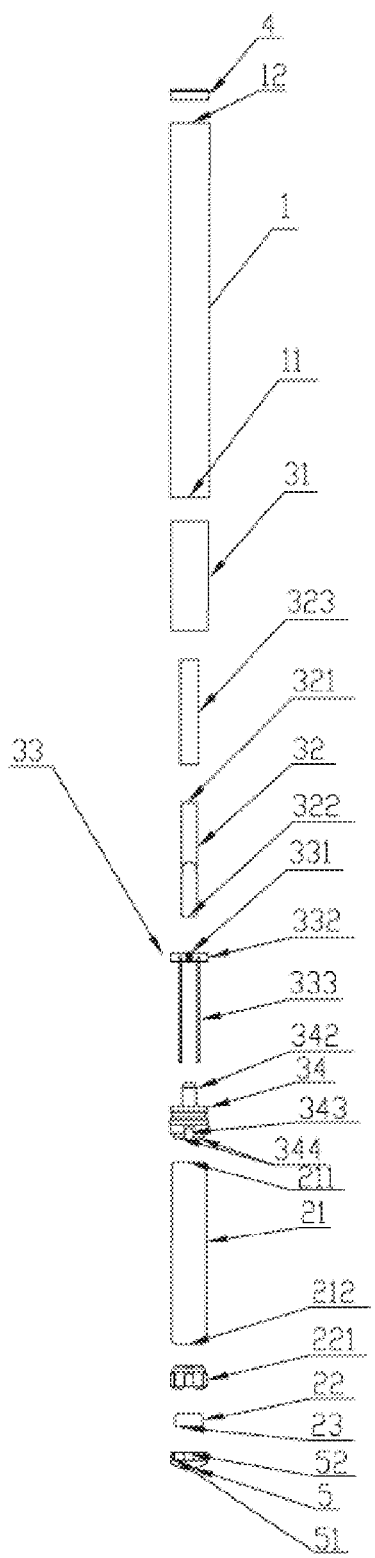
FIG. 1 is a schematic exploded view of a disposable electronic cigarette according to one embodiment.
Figure 2:
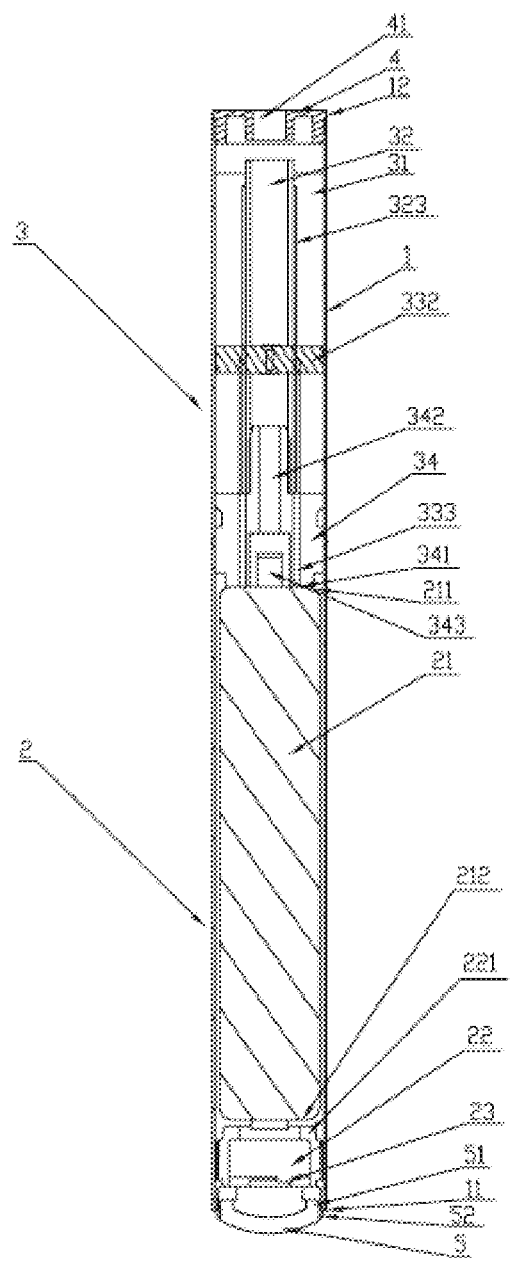
FIG. 2 is a schematic view of the disposable electronic cigarette according to one embodiment.
Figure 3:
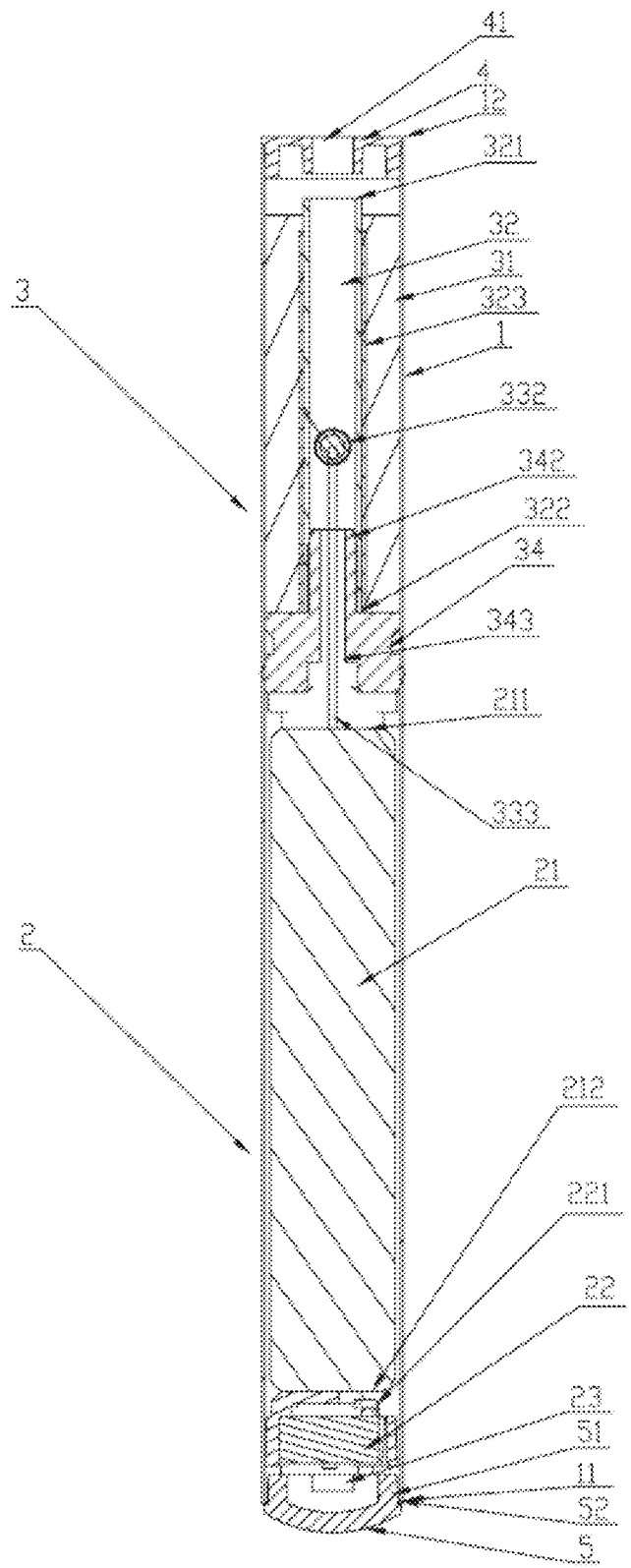
FIG. 3 is a cross-sectional view of the disposable electronic cigarette of FIG. 2.

FIGS. 1-3 illustratively show a disposable electronic cigarette according to a first embodiment, which includes a housing 1, a battery assembly 2, and an atomization device 3. The housing 1 is hollow, and includes two openings at two opposite ends thereof. The battery assembly 2 and the atomization device 3 are interconnected, and are arranged in the housing 1. In the present embodiment, the housing 1 is cylindrical.

As shown in FIGS. 7-8, 12-16, and 19, the atomization device 3 includes a liquid absorption member 31, a glass fiber tube 32, an electrical heating component 33, and a liquid stopper 34. The glass fiber tube 32 is hollow, and includes two openings at two opposite ends thereof. A hollow protruding rod 342 is arranged at a first end of the liquid stopper 34. The protruding rod 342 defines a through hole 343. The liquid stopper 34 includes a protruding stage 344 arranged at a second end thereof. The liquid stopper 34 defines a groove 345 along a circumferential direction in the outer surface thereof. The through hole 343 of the protruding rod 342 extends through the liquid stopper 34. The protruding rod 342 and the liquid stopper 34 are integrally formed. The liquid stopper 34 defines wire holes 341 at two opposite sides of the protruding rod 342. In the present embodiment, the liquid stopper 34 defines two wire holes 341. A first end 322 of the glass fiber tube 32 is connected with the protruding rod 342 of the liquid stopper 34. The electrical heating component 33 is mounted to the glass fiber tube 32. The electrical heating component 33 includes a heating wire 331, and a liquid-conducting core 332. The heating wire 331 is spirally wound around the liquid-conducting core 332. Two ends of the liquid-conducting core 332 pass through the sidewall of the glass fiber tube 32, and then extend outwardly in a horizontal direction. Two ends of the heating wire 331 are connected to conductive wires 333 respectively.

Two ends of the heating wire 331 are arranged at two opposite sides of the outer surface of the glass fiber tube 32. The conductive wires 333 pass through the wire holes 341 of the liquid stopper 34, and connect to the battery assembly 2. The outer surface of the glass fiber tube 32 is wrapped with the liquid absorption member 31. During wrapping process, because of uneven force exerted on the liquid-conducting core 332, the liquid-conducting core 332 forms a rod-shaped structure, a U-shaped structure, or an S-shaped structure. In the present embodiment, the liquid-conducting core 332 is rod-shaped. The liquid absorption member 31 has a structure of fibrous mesh. In the present embodiment, the liquid absorption member 31 is made of fiber cotton.

Figure 9:
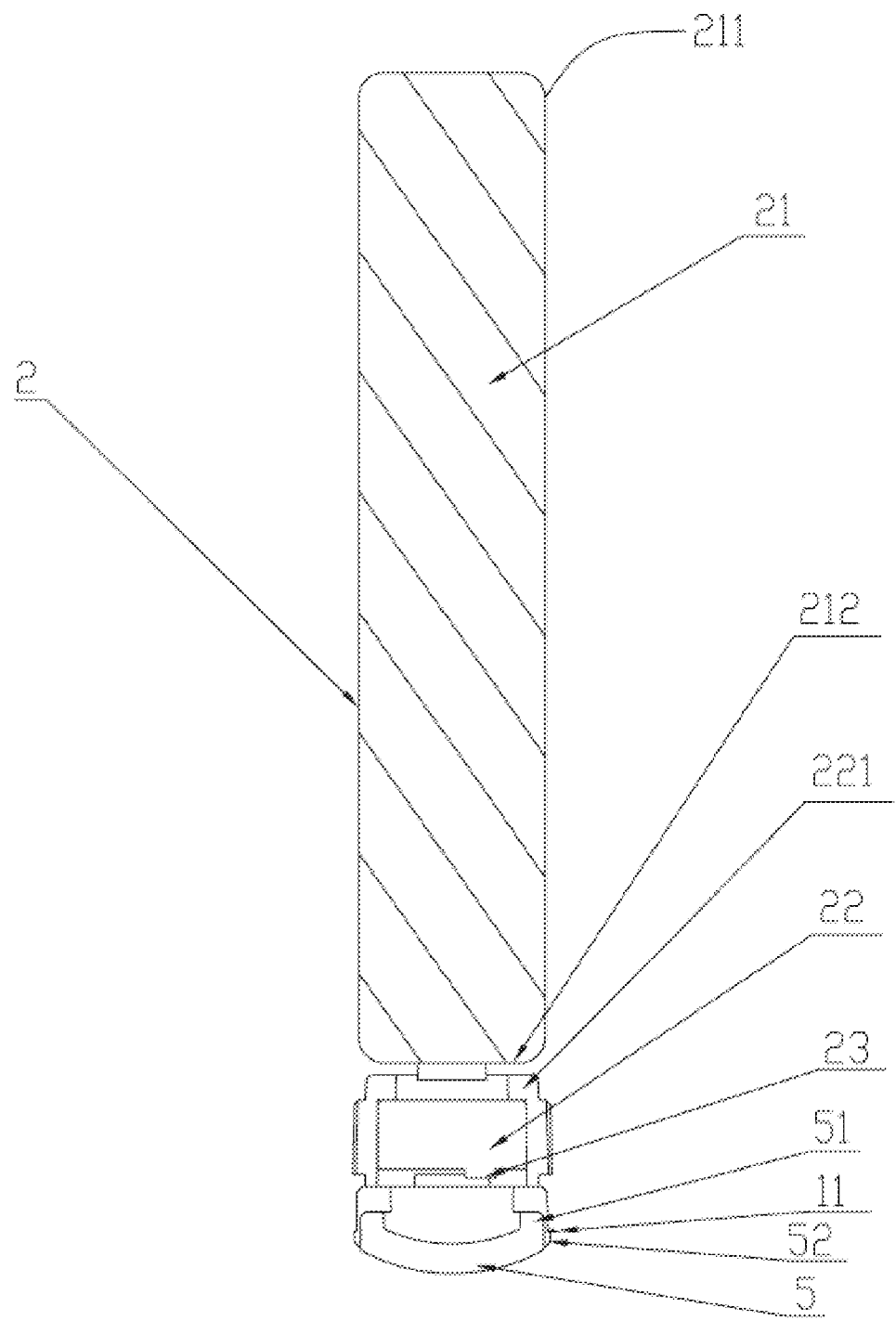
FIG. 9 is a schematic view of a battery assembly of the disposable electronic cigarette according to one embodiment.

As shown in FIG. 9, the battery assembly 2 includes a cell core 21, a controller 22, and a light emitting diode (LED) lamp 23. A diameter of the cell core 21 is less than that of the housing 1, so that air can flow smoothly along room formed between the cell core 21 and the housing 1. A first end of the cell core 21 is connected to the liquid stopper 34 via direct contact also referring to FIGS. 2, 10 and 11), a controller holder 221 is arranged at a second end 212 of the cell core 21, and the cell core 21 is connected with the controller 22 via direct contact. The controller 22 is disposed in the controller holder 221. The LED lamp 23 is arranged on the controller 22, and connected to the controller 22. The cell core 21 is model A02 aluminum-casing cell core, which is produced by Jiangxi Province Foster New Energy Co., Ltd. The controller 22 is model M15-63 controller produced by Huijin Technology Co., Ltd. of Dongguan City.

A mouthpiece cover 4 is arranged at second end 12 of the housing 1. The mouthpiece cover 4 defines a suction hole 41 therein, and the suction hole 41 faces a second end 321 of the glass fiber tube 32. A lampshade 5 is arranged at a first end 11 of the housing 1, and the lampshade 5 defines slots 52 in the side surface 51 thereof. In the present embodiment, the lampshade 5 defines two slots 52. The housing 1 is made of metal or plastic.

Figure 4:
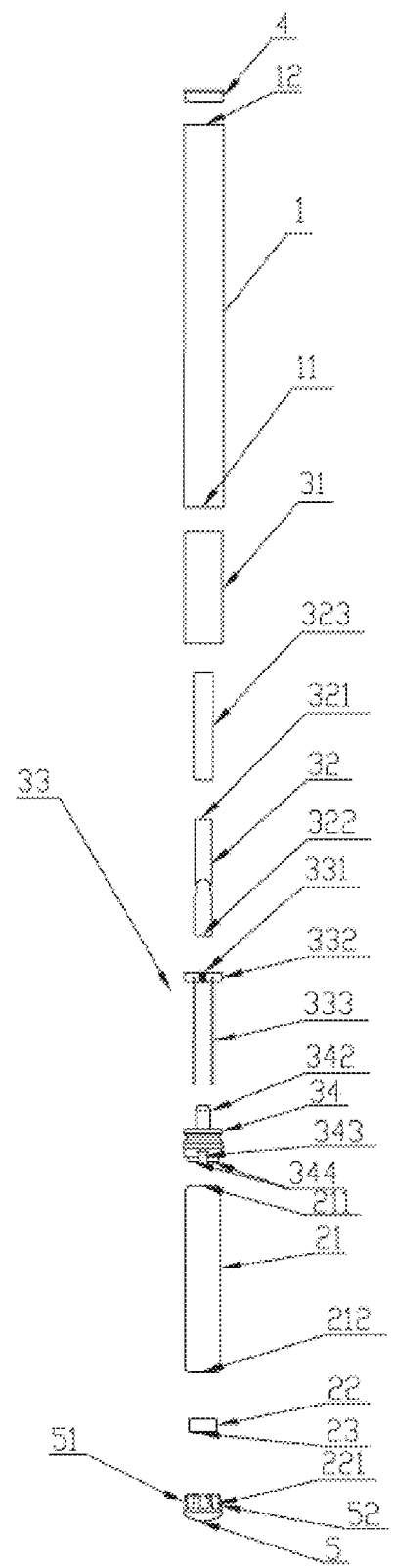
FIG. 4 is a schematic exploded view of a disposable electronic cigarette according to a second embodiment.
Figure 5:
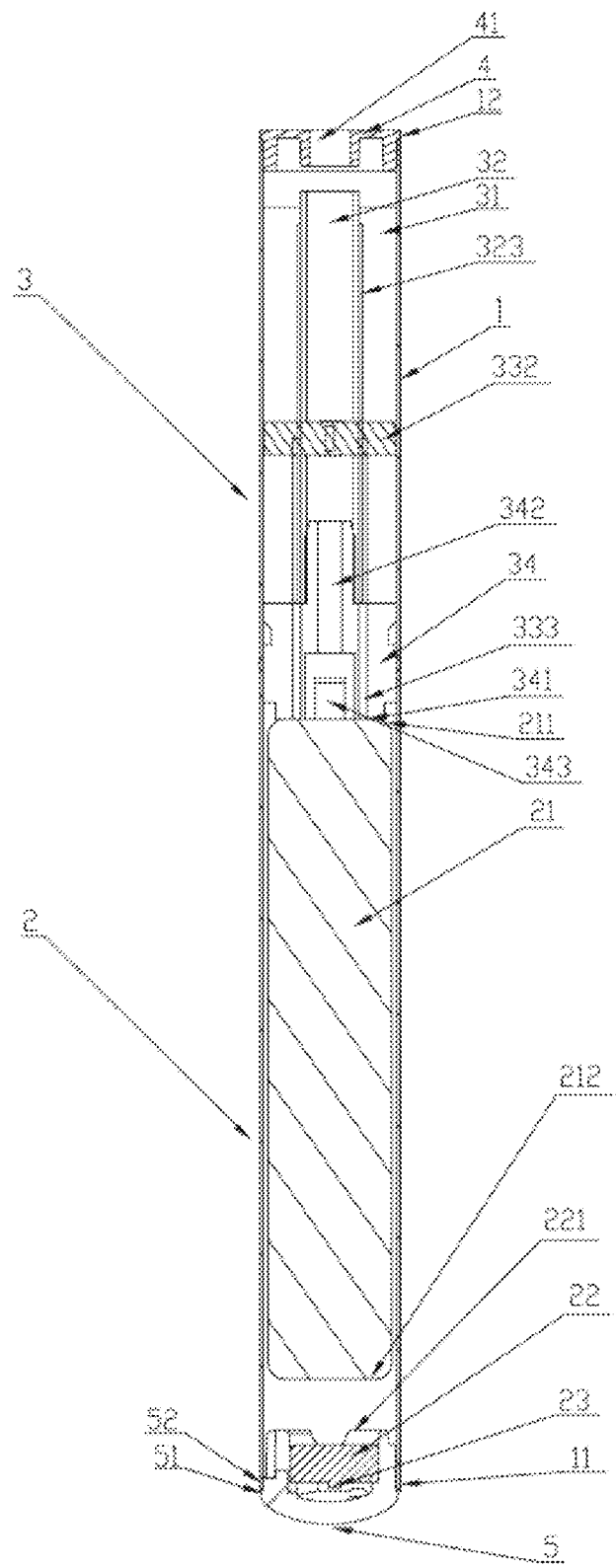
FIG. 5 is a schematic view of the disposable electronic cigarette according to the second embodiment.
Figure 6:
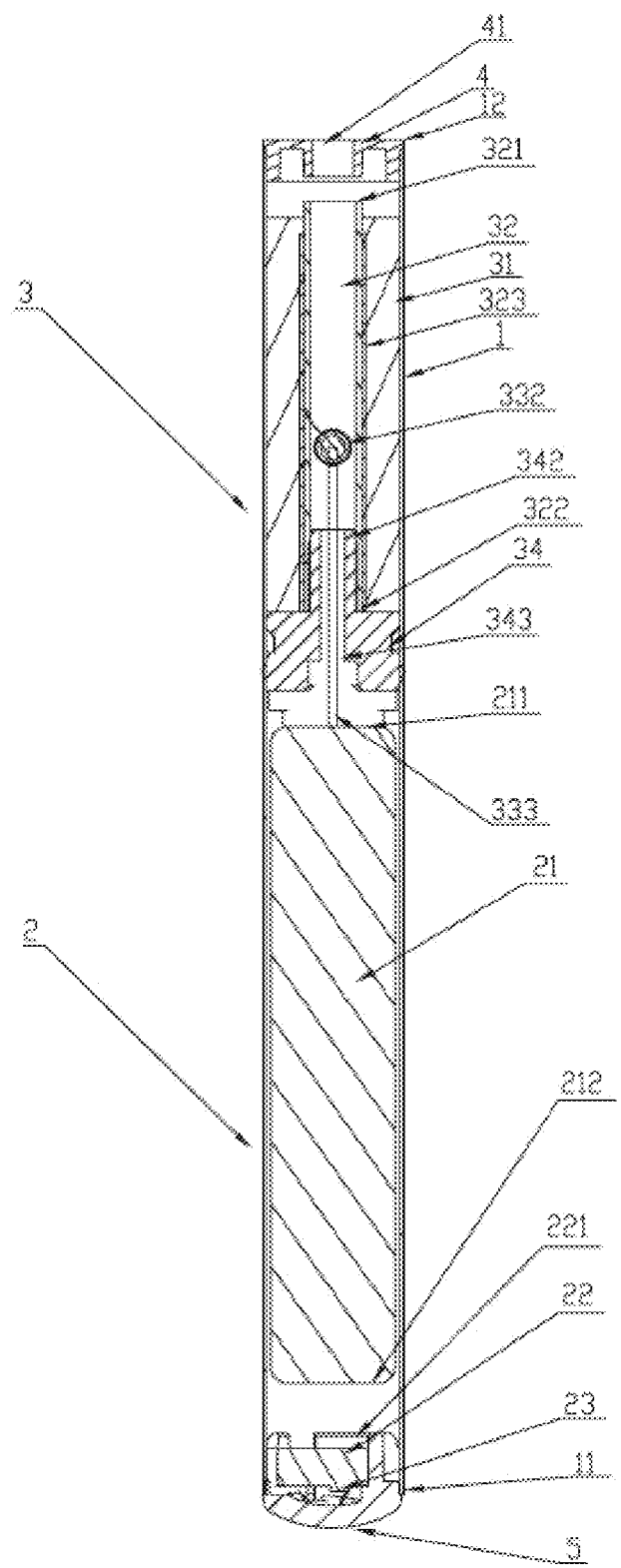
FIG. 6 is a cross-sectional view of the disposable electronic cigarette of FIG. 5.
Figure 7:
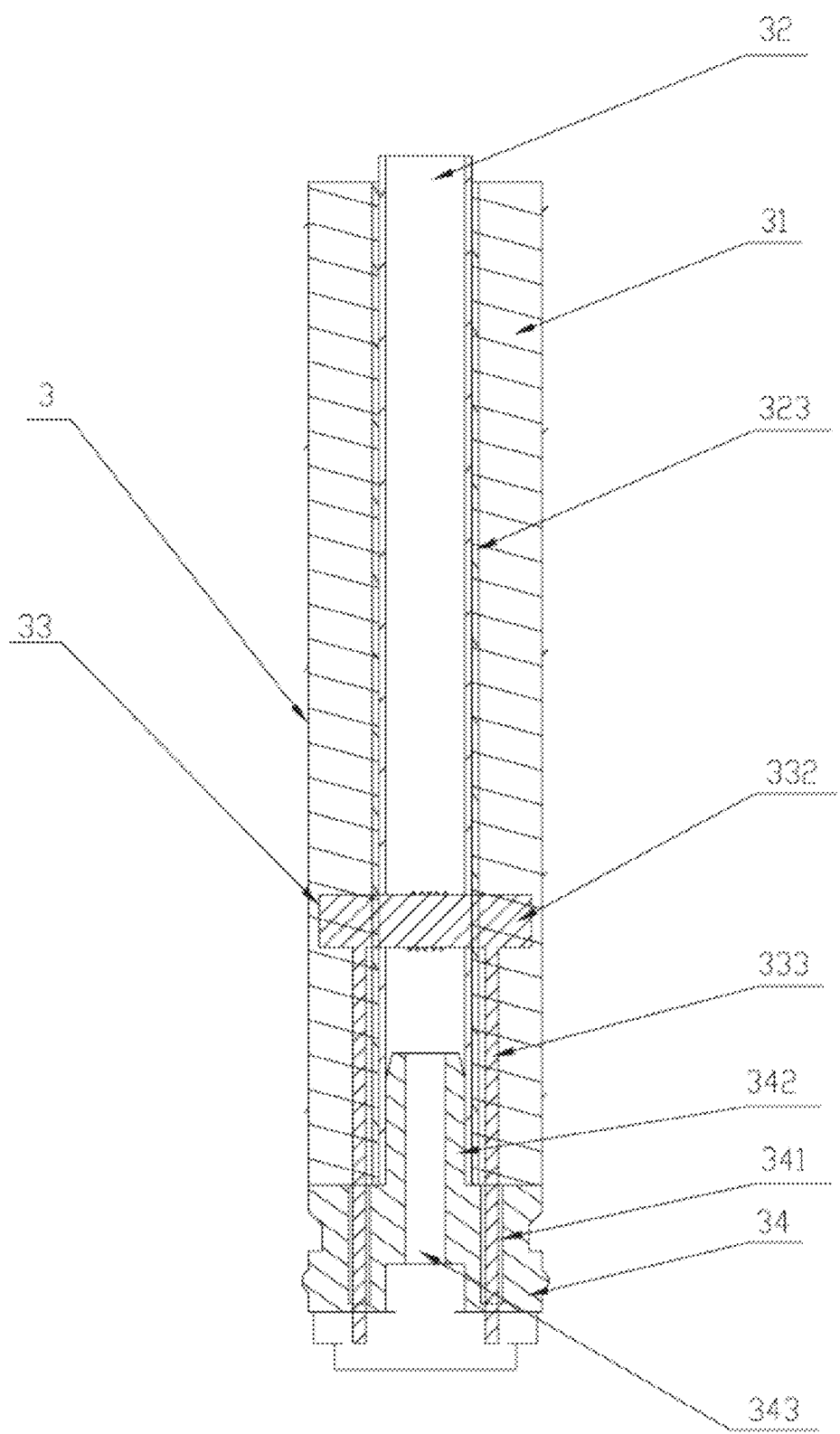
FIG. 7 is a schematic view of an atomization device of the disposable electronic cigarette according to one embodiment.
Figure 8:
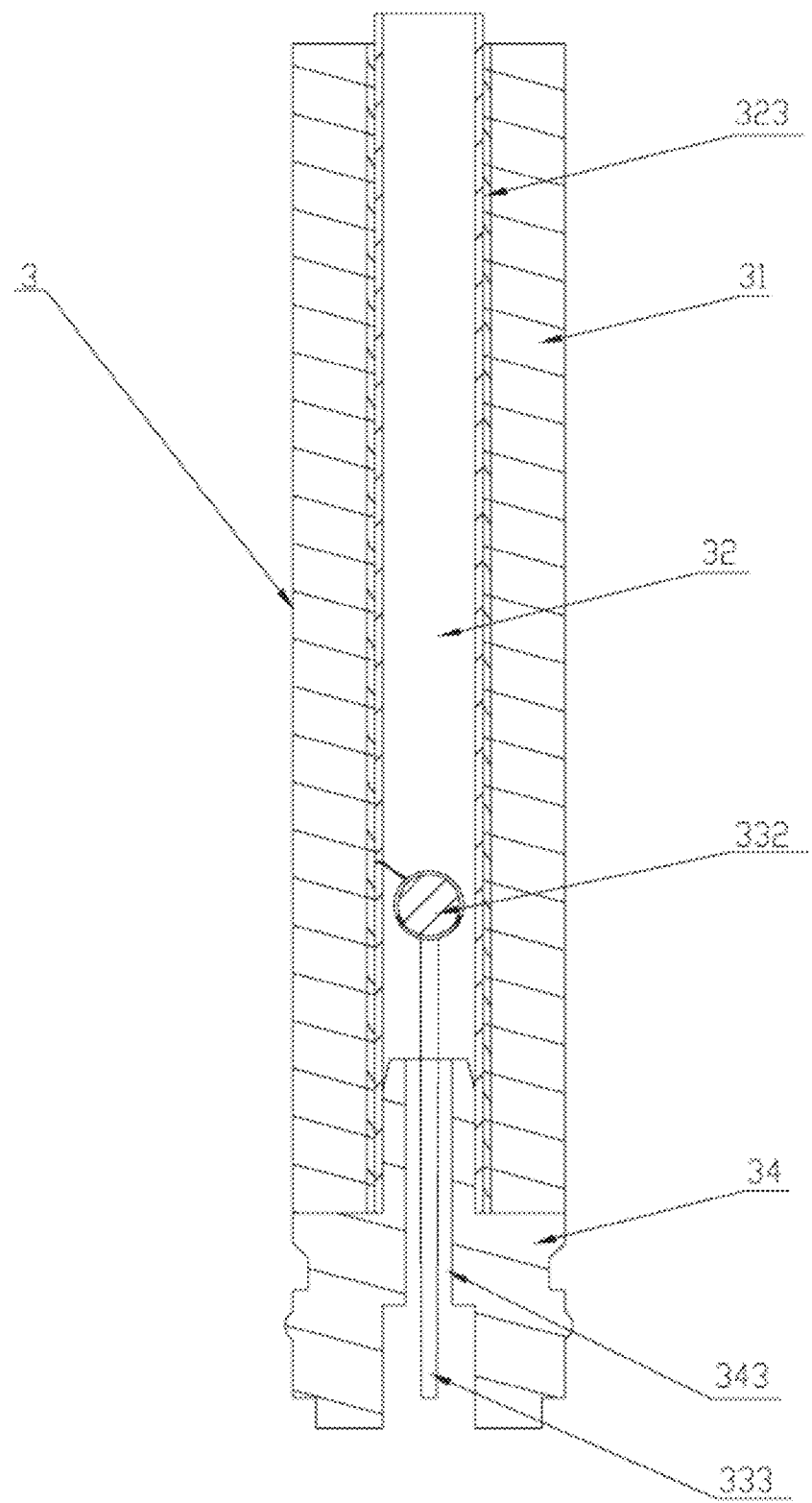
FIG. 8 is a cross-sectional view of the disposable electronic cigarette of FIG. 7.

FIGS. 4-6 illustratively show a disposable electronic cigarette in accordance with a second embodiment, which includes a housing 1, a battery assembly 2, and an atomization device 3. The housing 1 is hollow, and includes two openings at two opposite ends thereof. The battery assembly 2 and the atomization device 3 are connected, and disposed in the housing 1. The atomization device 3 includes a liquid absorption member 31, a glass fiber tube 32, an electrical heating component 33, and a liquid stopper 34. The glass fiber tube 32 is hollow, and defines two openings at two opposite ends thereof. The liquid stopper 34 includes a hollow cylindrical protruding rod 342 at a first end thereof. A through hole 343 defined in the protruding rod 342 extends through the liquid stopper 34. The liquid stopper 34 defines wire holes 341 at two opposite sides of the protruding rod 342. In the present embodiment, the liquid stopper 34 defines two wire holes 341. The electrical heating component 33 is mounted to the glass fiber tube 32. The electrical heating component 33 includes a heating wire 331, and a liquid-conducting core 332. The heating wire 331 is spirally wound around the liquid-conducting core 332.

A mouthpiece cover 4 is set at a second end 12 of the housing 1. A suction hole 41 is defined in the mouthpiece cover 4, and the suction hole 41 faces toward a second end 322 of the glass fiber tube 32.

Figure 10:
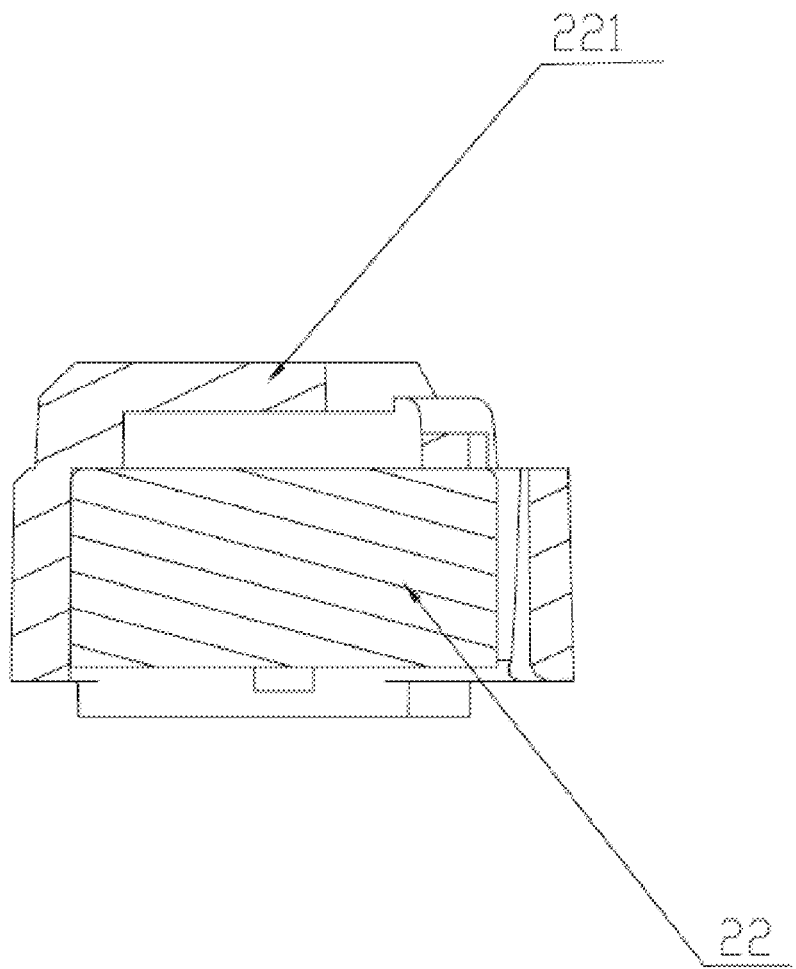
FIG. 10 is a cross-sectional view, showing the engagement of a controller and a controller holder of the disposable electronic cigarette according to the second embodiment.
Figure 11:
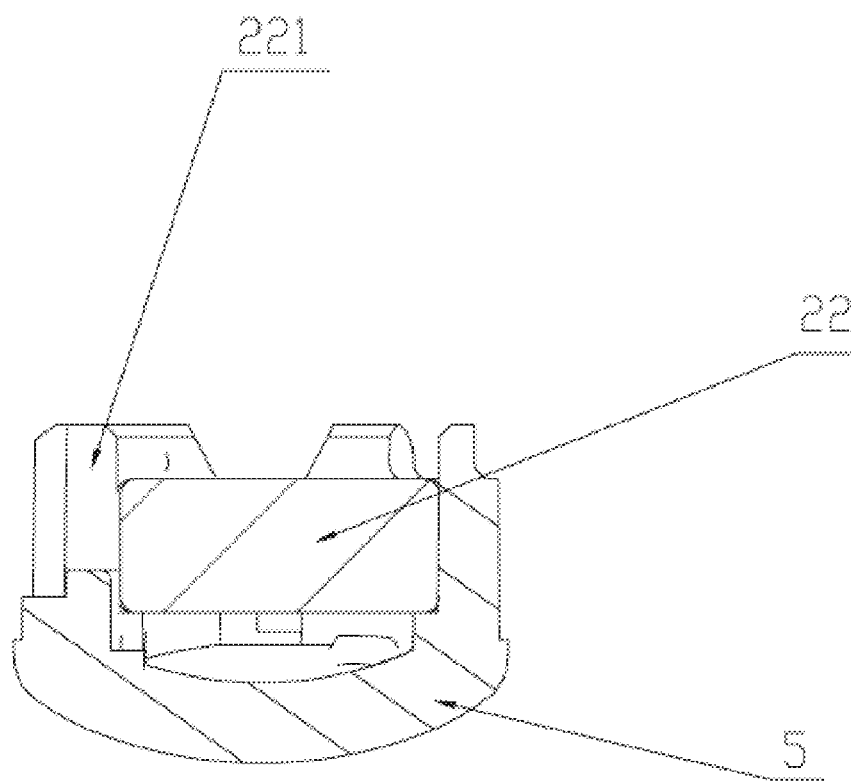
FIG. 11 is a cross-sectional view, showing a controller holder and a lampshade integrally formed in the disposable electronic cigarette according to the second embodiment.
Figure 12:
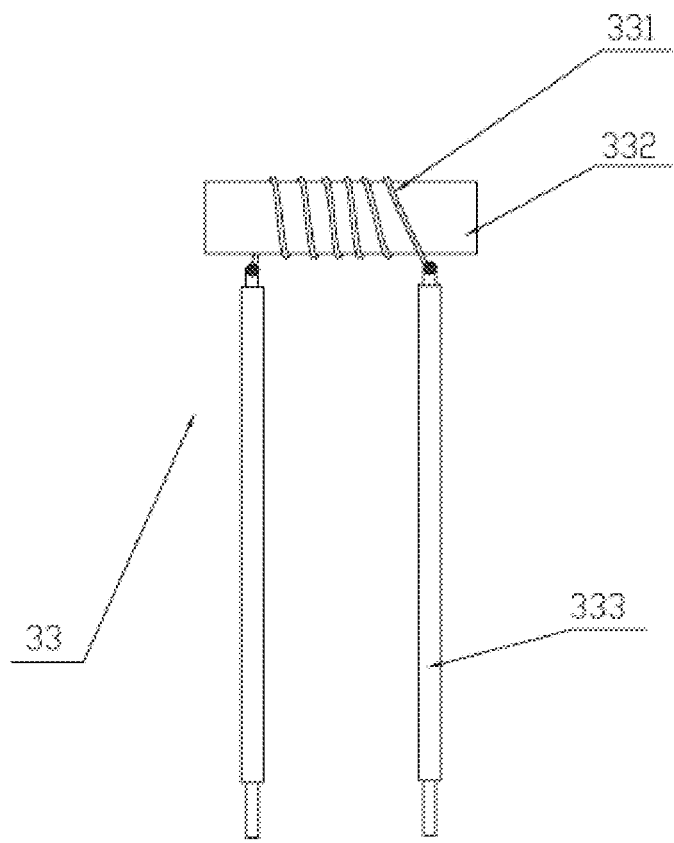
FIG. 12 is a schematic view of an electrical heating component of the disposable electronic cigarette according to one embodiment.
Figure 13:
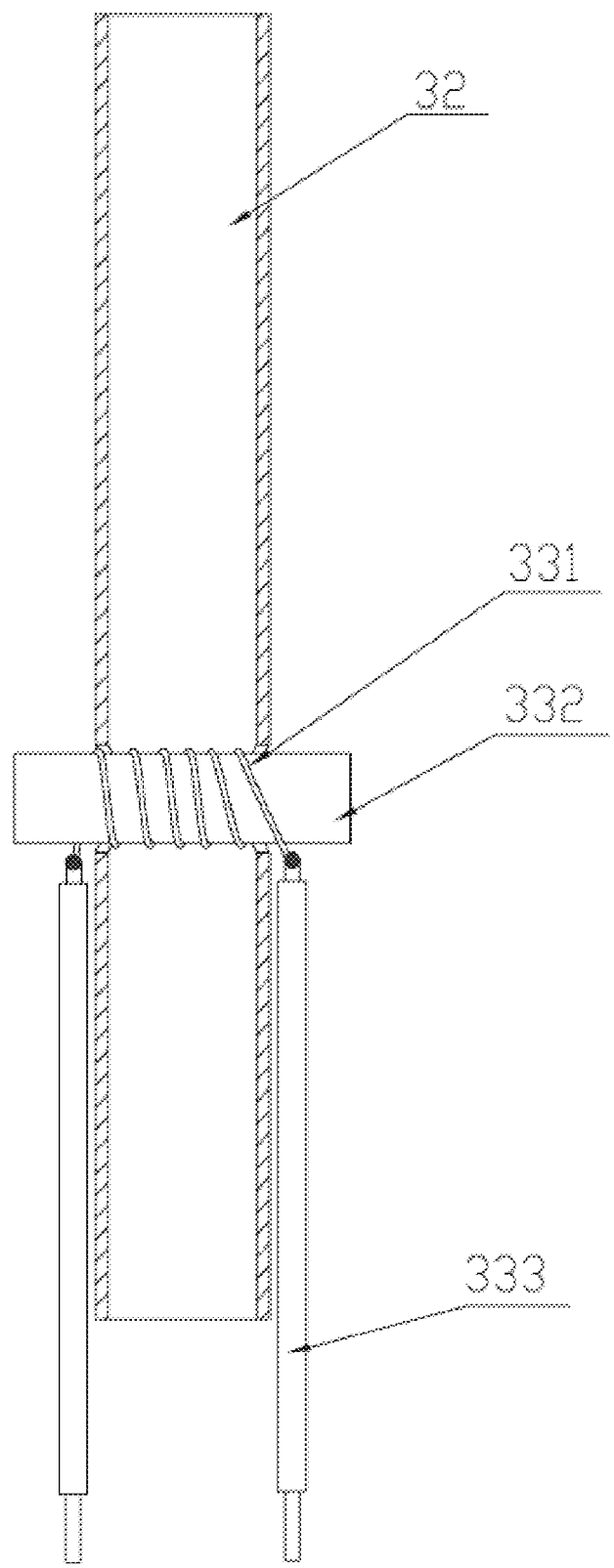
FIG. 13 is a schematic view, showing a first engagement between the electrical heating component and a glass fiber tube of the disposable electronic cigarette according to one embodiment.
Figure 14:
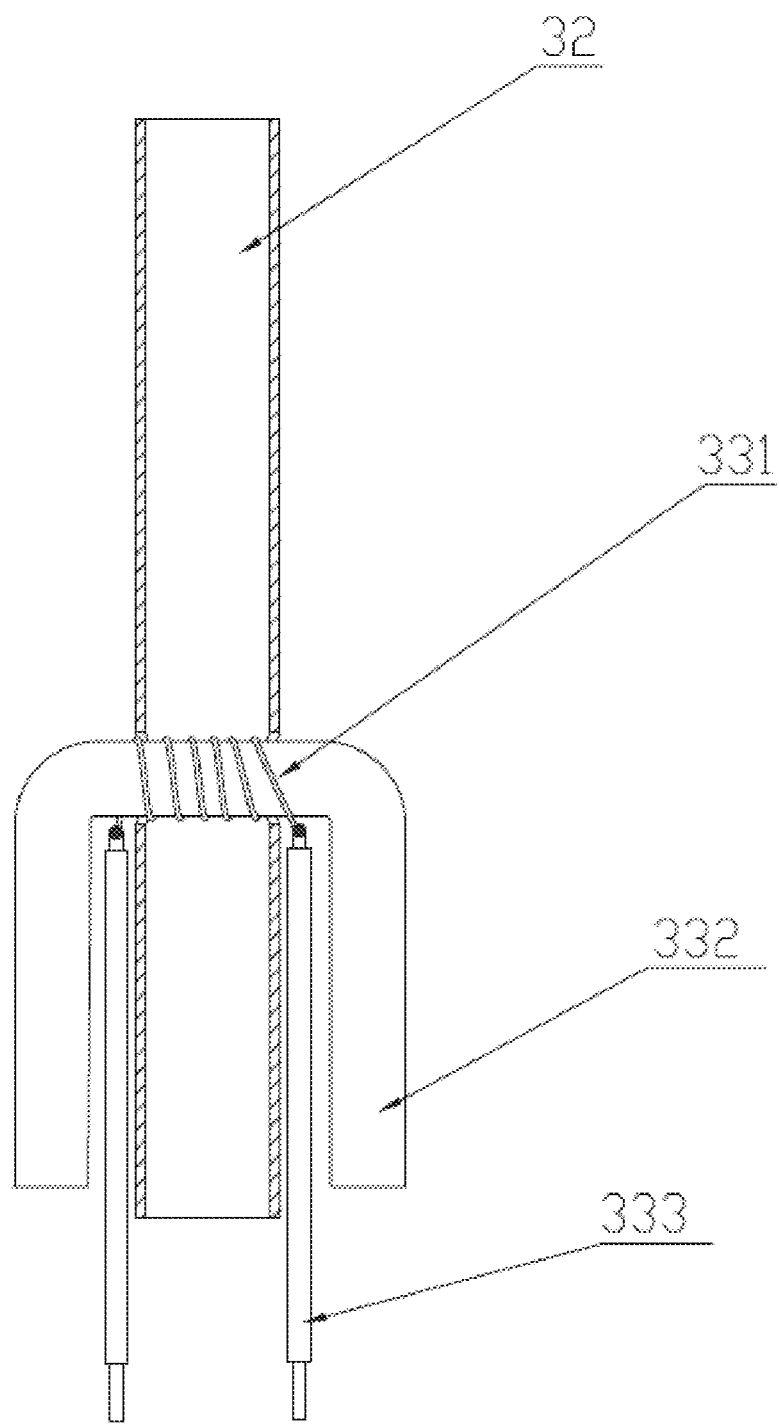
FIG. 14 is a schematic view, showing a second engagement between the electrical heating component and the glass fiber tube of the disposable electronic cigarette according to one embodiment.
Figure 15:
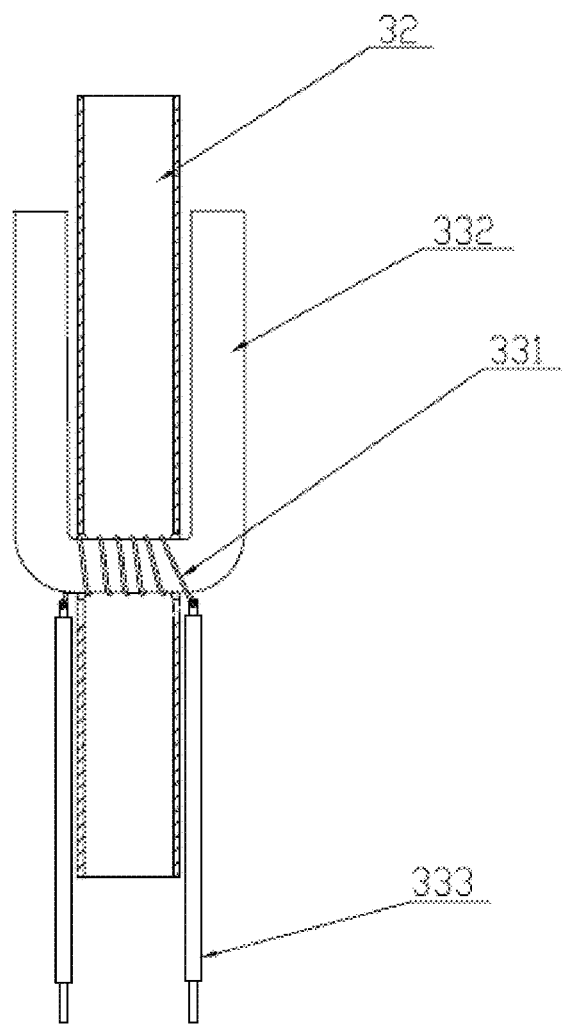
FIG. 15 is a schematic view, showing a third engagement between the electrical heating component and the glass fiber tube of the disposable electronic cigarette according to one embodiment.
Figure 16:
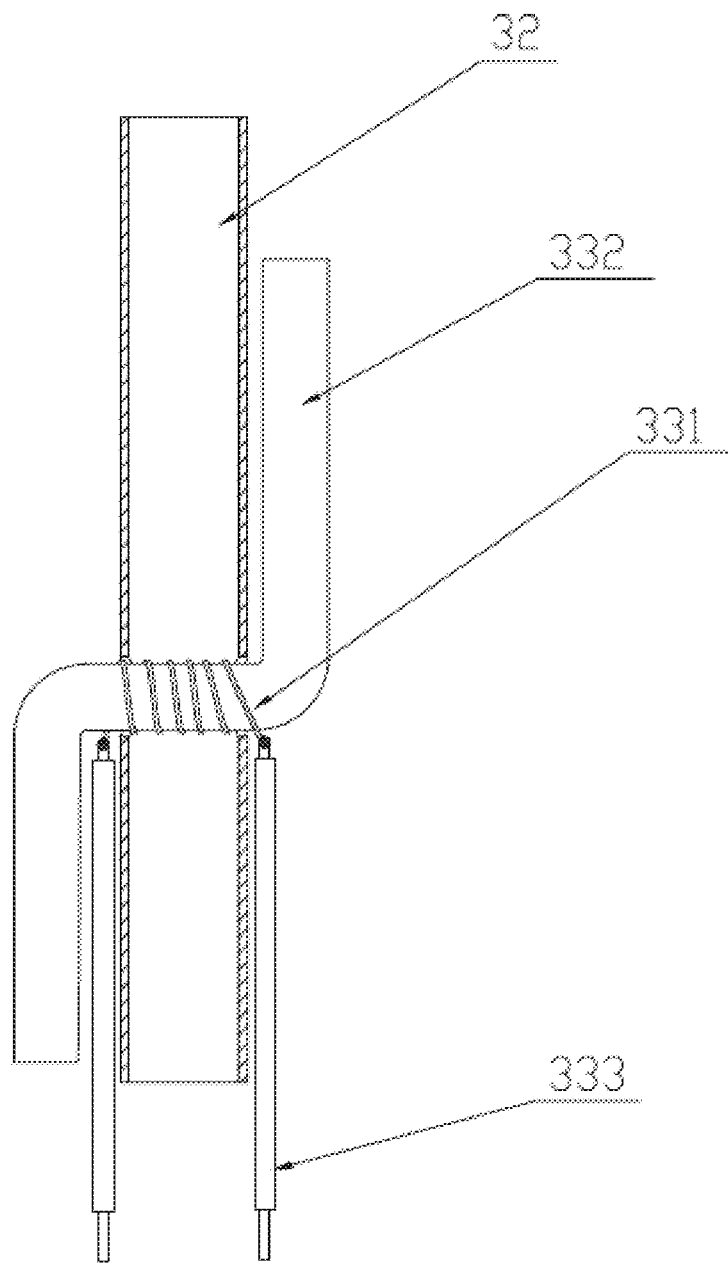
FIG. 16 is a schematic view, showing a fourth engagement between the electrical heating component and a glass fiber tube of the disposable electronic cigarette according to one embodiment.

As shown in FIGS. 10 and 11, the differences from the second embodiment are that the controller 22 is arranged in the controller holder 221, the lampshade 5 is connected with the controller holder 221, and accordingly, the controller holder 221 accommodates the controller 22 therein. The lampshade 5 and the controller holder 221 are integrally formed, and the controller 22 is received in the lampshade 5 and the controller holder 221.

Figure 17:
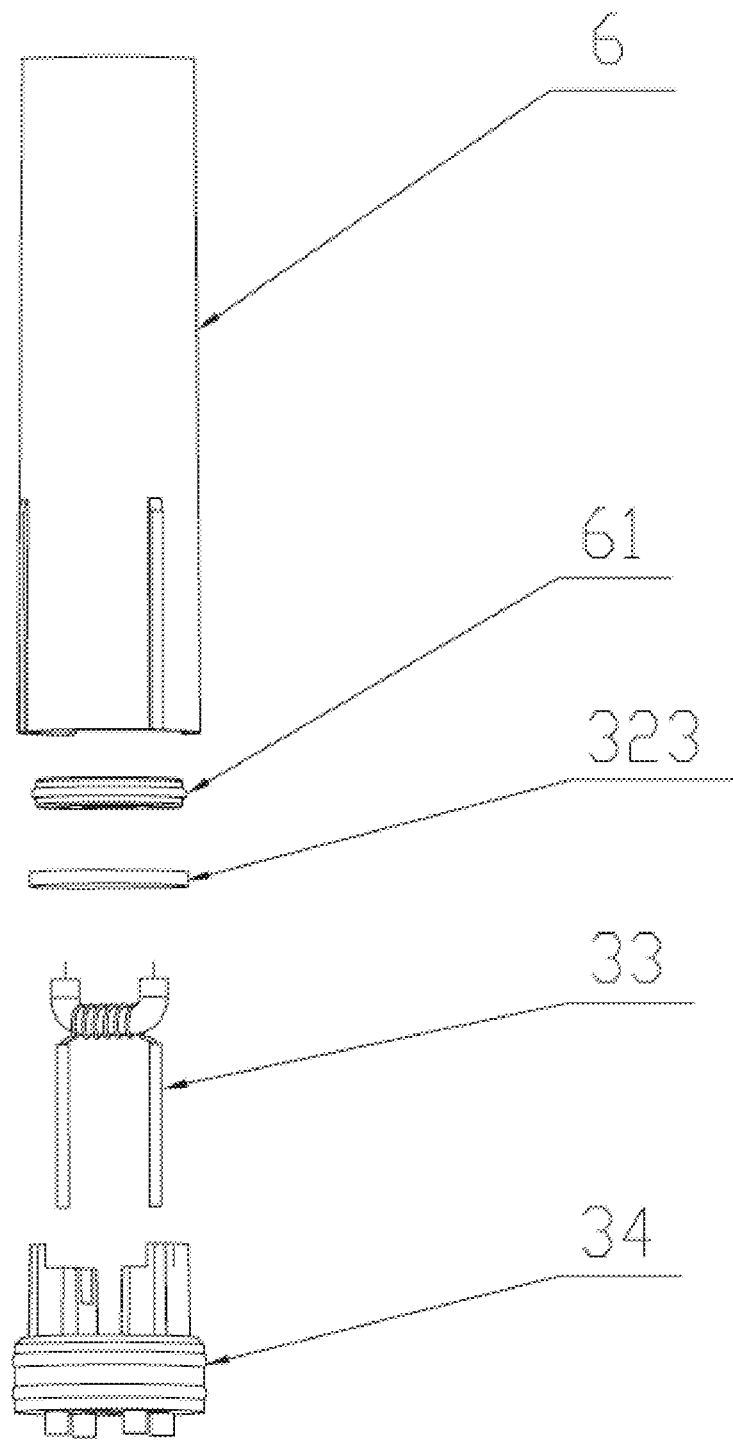
FIG. 17 is an exploded view of an atomization device of a disposable electronic cigarette according to a third embodiment.
Figure 18:
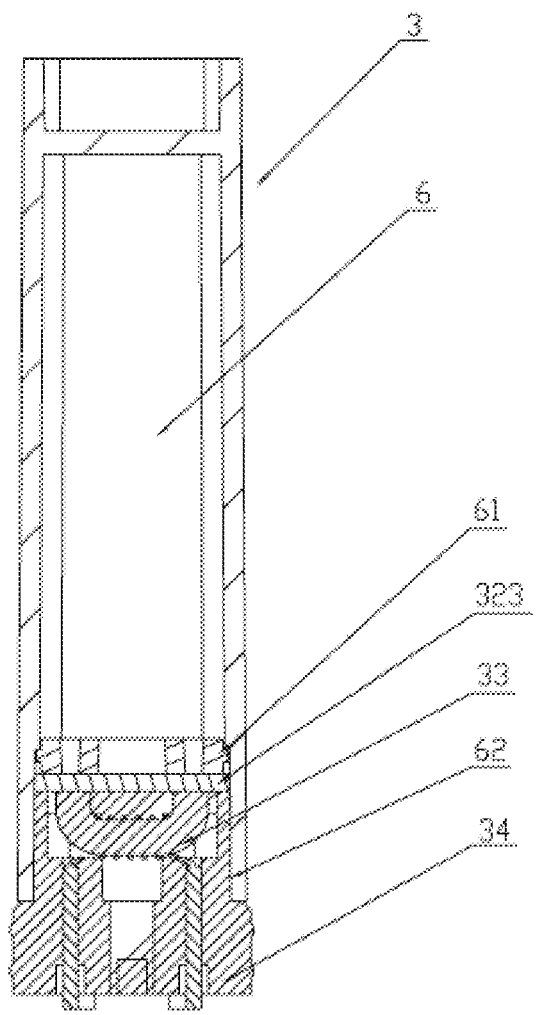
FIG. 18 is a schematic view of the disposable electronic cigarette according to the third embodiment.
Figure 19:
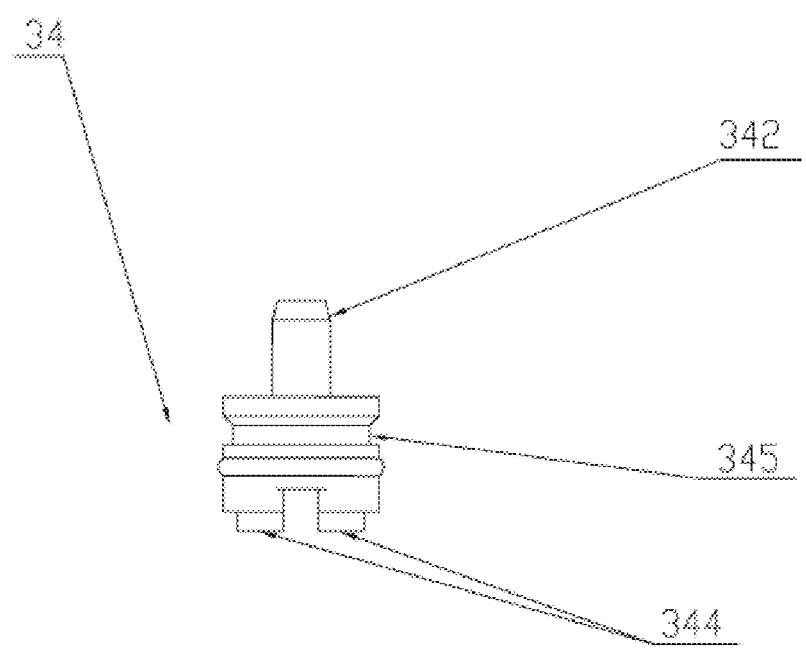
FIG. 19 is a schematic view of a liquid stopper of the disposable electronic cigarette according to one embodiment.

FIGS. 17 and 18 illustratively show an atomization device of a disposable electronic cigarette according to a third embodiment. The atomization device 3 includes a liquid tank 6, a liquid guide device, an electrically heating component 33, and a liquid stopper 34. The liquid guide device includes a liquid tank cushion 61 and a cotton cloth 323. The liquid tank 6 is disposed on the liquid tank cushion 61. The liquid tank cushion 61 is arranged on the cotton cloth 323. The cotton cloth 323 is disposed on the liquid stopper 34. The liquid stopper 34 is airtight connected to an end 62 of the liquid tank with an opening. The electrically heating component 33 is arranged at the end 62 of the liquid tank, and engaged in the liquid stopper 34 by snap-fit.

When a smoker inhales air through suction hole 41 of the mouthpiece cover 4 at the second end 12 of the housing 1, air enters the housing 1 through the slots 52 in the side surface of the lampshade 5 at the first end 11 of the housing. After the air passes a sensing area at a front end of the controller 22, the controller 22 sends a signal to the cell core 21, and then the electrically heating wire 331 and the LED lamp 23 are powered on. The LED lamp 23 is powered on, and emits light simulating smoking flame. After the electrically heating wire 331 is powered on, the liquid-conducting core 332 is heated. When the liquid-conducting core 332 reaches the vaporization temperature of tobacco liquid, the tobacco liquid in the liquid-conducting core 332 begin to vaporize, and form an aerosol. The tobacco liquid in the liquid-absorption component 31 is conveyed to the liquid-conducting core 332 through the cotton cloth 323. The aerosol flows along the glass fiber tube 32, and then passes through the suction hole 41 of the mouthpiece cover 4 to the mouth of the smoker. In this process, the time it takes to vaporize the tobacco liquid is short. Thus, the generation of the aerosol and the illumination of the LED lamp are almost synchronous. That is to say, when the LED lamp is illuminated, the aerosol is generated, and can be inhaled into the mouth of the smoker.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. A disposable electronic cigarette, comprising a unitary housing, a battery assembly, and an atomization device, the housing being hollow and comprising openings at two opposite ends thereof, the battery assembly and the atomization device being connected and disposed in the unitary housing;

wherein the atomization device comprises a liquid absorption member, a glass fiber tube, an electrically heating component and a liquid stopper, the glass fiber tube is hollow and defines openings at two opposite ends thereof, the atomization device further comprises a hollow protruding rod, the protruding rod is arranged at a first end of the liquid stopper, the protruding rod defines a through hole, the through hole extends through the liquid stopper, the stopper comprises a protruding stage at a second end thereof, the liquid stopper defines a groove along a circumferential direction thereof, the electrically heating component is mounted to the glass fiber tube, a first end of the glass fiber tube is connected with the protruding rod of the liquid stopper such that the protruding rod fits inside the glass fiber tube, and an outer surface of the glass fiber tube is wrapped with the liquid absorption member.

2. The disposable electronic cigarette of claim 1, wherein the liquid guide comprises a liquid tank cushion, and a cotton cloth, the liquid tank is disposed on the liquid tank cushion, the liquid tank cushion is arranged on the cotton cloth, the cotton cloth is disposed on the liquid stopper, the liquid tank defines an opening at an end thereof, the liquid stopper is airtight connected to the end of the liquid tank, the electrically heating component is arranged at the end of the liquid tank, and engaged in the liquid stopper.

3. The disposable electronic cigarette of claim 1, wherein the liquid stopper defines wire holes at two opposite sides of the protruding rod.

4. The disposable electronic cigarette of claim 1, wherein the protruding rod and the liquid stopper are integrally formed.

5. The disposable electronic cigarette of claim 1, wherein the electric heating component comprises a heating wire, and a liquid-conducting core, the heating wire is spirally wound around the liquid-conducting core, two ends of the liquid-conducting core pass through a sidewall of the glass fiber tube, and then extend outwardly in a horizontal direction, two ends of the heating wire are connected to conductive wires, the conductive wires pass through the wire holes of the liquid stopper, and connect to the battery assembly.

6. The disposable electronic cigarette of claim 5, wherein the liquid-conducting core has a rod-shaped structure, a U-shaped structure, or an S-shaped structure.

7. The disposable electronic cigarette of claim 1, wherein the liquid absorption member has a structure of fibrous mesh.

8. A disposable electronic cigarette, comprising a housing, a battery assembly, and an atomization device, the housing being hollow and comprising openings at two opposite ends thereof, the battery assembly and the atomization device being connected and disposed in the housing, wherein the atomization device comprises a liquid absorption member, a glass fiber tube, an electrically heating component and a liquid stopper, the liquid stopper is engaged at one end of the glass fiber tube, and the electrically heating component is disposed in the glass fiber tube while the liquid absorption member is disposed outside and around the glass fiber tube, wherein the battery assembly comprises a cell core, a controller, and an LED (light emitting diode) lamp, a first end of the cell core is connected with the liquid stopper via direct contact, a second end of the cell core is connected with the controller via direct contact, and the LED lamp is disposed on the controller.

9. The disposable electronic cigarette of claim 8, further comprising a controller holder, wherein the controller is arranged in the controller holder, and the controller holder is arranged at the second end of the cell core.

10. The disposable electronic cigarette of claim 1, further comprising a lampshade at a first end of the housing, wherein the lampshade defines slots in a side surface thereof.

11. The disposable electronic cigarette of claim 10, wherein the lampshade and the controller holder are integrally formed.

12. The disposable electronic cigarette of claim 6, further comprising a mouthpiece cover at a second end of the housing, wherein the mouthpiece cover defines a suction hole, the suction hole faces a second end of the glass fiber tube.

13. The disposable electronic cigarette according to claim 1, wherein the housing is made of metal or plastic.

14. The disposable electronic cigarette of claim 8, wherein a diameter of the cell core is less than that of the housing.

15. A disposable electronic cigarette, comprising a unitary housing, a battery assembly, and an atomization device, the housing being hollow and comprising openings at two opposite ends thereof, the battery assembly and the atomization device being connected and disposed in the unitary housing;

wherein the atomization device comprises a liquid absorption member, a glass fiber tube, an electrically heating component and a liquid stopper, an outer surface of the glass fiber tube is wrapped with the liquid absorption member the electric heating component is received in the glass fiber tube and comprises a heating wire and a liquid-conducting core, the heating wire is spirally wound around the liquid-conducting core, and two ends of the liquid-conducting core pass through sidewalls of the glass fiber tube, respectively, to extend outwardly and to be exposed outside the glass fiber tube.

* * * * *